United States Patent

Schunk et al.

[11] Patent Number: 6,012,268
[45] Date of Patent: Jan. 11, 2000

[54] METHOD OF PRODUCING PRODUCTS FROM POLYMER MATERIALS HAVING A MEDICAMENTOUS DEPOT EFFECT

[75] Inventors: Werner Schunk; Gerhard Merkmann; Konrad Giessmann, all of Gotha; Hans-Josef Ludwig, Gelnhausen; Wilfried Mertens, Bad Orb, all of Germany

[73] Assignee: Veritas Gummiwerke AG, Gelnhausen, Germany

[21] Appl. No.: 08/930,626

[22] PCT Filed: Jul. 25, 1995

[86] PCT No.: PCT/EP95/02943

§ 371 Date: May 12, 1998

§ 102(e) Date: May 12, 1998

[87] PCT Pub. No.: WO96/35459

PCT Pub. Date: Nov. 14, 1996

[30] Foreign Application Priority Data

May 10, 1995 [DE] Germany ............... 195 17 167

[51] Int. Cl.⁷ ........................ B65B 55/12
[52] U.S. Cl. ............... 53/428; 53/425; 53/111 R
[58] Field of Search ............. 53/425, 428, 111 R, 53/122; 422/22, 23, 24

[56] References Cited

U.S. PATENT DOCUMENTS

| | | | |
|---|---|---|---|
| 3,907,732 | 9/1975 | Maruyama et al. | 260/22 |
| 3,994,686 | 11/1976 | Rauser et al. | 21/102 R |
| 4,566,927 | 1/1986 | Wood | 156/203 |
| 4,652,763 | 3/1987 | Nablo | 250/492.3 |
| 5,225,236 | 7/1993 | Keusch et al. | 428/77 |
| 5,260,848 | 11/1993 | Childers | 361/127 |
| 5,681,883 | 10/1997 | Hill et al. | 524/404 |
| 5,827,293 | 10/1998 | Elliott | 606/107 |

*Primary Examiner*—Joseph J. Hail, III
*Assistant Examiner*—William Hong
*Attorney, Agent, or Firm*—Finnegan, Henderson, Farabow, Garrett & Dunner, L.L.P.

[57] ABSTRACT

A method of producing products from polymer materials having a medicamentous depot effect, characterized by the steps of: mixing the starting materials; shaping the mixture into a desired mold; introducing the resultant mold into a protective packaging; and curing and sterilizing the mold in the protective packaging.

19 Claims, No Drawings

METHOD OF PRODUCING PRODUCTS FROM POLYMER MATERIALS HAVING A MEDICAMENTOUS DEPOT EFFECT

BACKGROUND OF THE INVENTION

The present invention relates to a method of producing products from polymer materials having a medicamentous depot effect for use in the medical field in or on the human organism.

The preparation of products from polymer materials for medical uses with the aid of conventional curing methods, namely by hot-air, steam or UHF methods or by LCM methods (liquid curing methods), is already known. Polymer products having a medicamentous depot effect cannot be produced with the aid of these methods because of a great thermal load.

Furthermore, patent specification DE 37 41 342 discloses a method for producing a medicinal material with a high antithrombogenicity, which material is inter alia suited for catheters and other medicinal instruments that come into contact with tissues and flowing blood. The described material can be produced by polymerization of a methacrylamide derivative with a tertiary amino group or a hydrophilic monomer with a copolymerization-accelerating characteristic on a high-molecular polyolefin or polyurethane substrate. Active spots are produced on the substrate through ionizing radiation. The active substrate is subsequently immersed into a solution of a monomer. The antithrombogenic effect of the material is consequently due to the grafted monomer.

As becomes apparent from the above, the material with the antithrombogenic effect can only be fixed to the substrate superficially in the known prior art. As a consequence, it is not possible to ensure a long-lasting and continuous release of the biologically active substance that would be controllable via concentration drop. Furthermore, this publication does not hint at any biological activity of the finished products.

Furthermore, DD 275697 discloses a method of producing tubes for medicinal uses that contain biologically active polymer materials. β-rays are used for curing, and metal oxides, such as ZnO or $TiO_2$ as curing activators. Although this method avoids extremely high temperature loads as are caused by conventional methods, there are other disadvantages. For instance, relatively high radiation doses which, in turn, produce a considerable amount of reaction heat are required for curing. To eliminate the reaction heat, the tubes must therefore be pulled over steel mandrels prior to curing and, after confection and packaging, they must be subjected to a separate sterilization process which, on the one hand, increases the production costs and, on the other hand, jeopardizes the continuance of the biological activity beyond the production process, for it is known that high heat and/or radiation loads impair the biological activity of organic compounds. Moreover, the metal oxides ZnO and $TiO_2$ that are used as activators must be classified as toxic and therefore as detrimental to the body.

It is therefore the object of the present invention to provide a method of producing products from polymer materials having a medicamentous depot effect, the method overcoming the drawbacks of the known prior art and being adapted to be carried out at low costs.

SUMMARY OF THE INVENTION

This object is achieved according to the invention by a method of producing polymer materials having a medicamentous depot effect, the method being characterized by the steps of:

mixing the starting materials,
shaping the mixture into a specific mold,
introducing the resultant mold into a protective packaging, and
curing and sterilizing the mold in the protective packaging.

DETAILED DESCRIPTION OF THE INVENTION

It is possible with the method of the invention to combine the process steps curing and sterilization, whereby the method can be performed in a much easier and more rapid manner. Furthermore, it has been found that the additional heat or radiation load which is normally observed during sterilization can be avoided by combining the process steps curing and sterilization. It is thereby ensured that the biological activity of the products is fully maintained and not jeopardized, especially during the production process. Furthermore, the method of the invention can be carried out at low costs.

It has been found to be an advantage when curing and sterilization are performed by electron radiation, with radiation doses of 10 to 120 KGy, preferably 20 to 66 KGy, being used.

The β-rays effect both curing of the material and sterilization thereof. The indicated radiation doses have turned out to be especially preferred values at which the formation of large heat amounts can be prevented and the properties of the products are not affected disadvantageously.

Depending on the respective needs, the polymer material may have added thereto substances which act as activators and curing agents to reduce the radiation dose. Acrylates are especially preferred as activating and curing substances. The addition of trimethylolpropane trimethacrylate is especially preferred.

The addition of these substances which simultaneously act as activators and curing agents in radiation curing leads to a high and uniform curing yield over the whole volume of the polymer material with the medicamentous depot effect and simultaneously guarantees a curing action at small radiation doses.

Methacrylates and the derivatives thereof have turned out to be especially suited for curing the base polymer for biologically active materials, since they neither influence the biologically active substance contained in the base polymer with respect to the activity thereof, nor do they fix the active substance on or in the base polymer, which would impede the intended movability thereof as for releases to media flowing by.

Furthermore, a biologically active substance may be mixed with the polymer material. In so doing, the biologically active substance may already be bound to an inorganic or organic carrier prior to mixing with the polymer material, for instance to molecular sieves and/or layered silicates.

In introducing a biological substance into the polymer material, it is possible to achieve a permanent inclusion thereof. A substrate preferably serves as a depot, permitting the continuous release thereof to the surrounding liquid media in a particular case, depending on the prevailing concentration drop.

To further reduce the harmful heat amounts occurring during curing, the molded polymer material is preferably inserted into a heat-conducting mold after introduction into the protective cover and prior to curing and sterilization. The resultant low reaction heat is removed through this heat-conducting mold, whereby the accumulation of heat is prevented.

The following mixing ingredients have turned out to be especially suited as starting materials for polymer materials:

Natural rubber, chalk, curing activator, molecular sieve/medicament adduct or silicone rubber, chalk, molecular sieve/medicament adduct.

With these compositions, it is possible to dispense with the metal oxides ZnO and $TiO_2$ that must be classified as toxic, to avoid side reactions of the additives with the biologically active substance during radiation and to exclude toxic activities by further additives during application. Furthermore, the necessary stability and processability can be achieved without flow or stabilization aids, such as stearic acid and factice, through the selection of polymers and their pretreatment and through the increased dosage of the toxically harmless chalk as a filler.

The mixture of the invention exhibits adequate stability, so that the steel mandrel which has so far been in general use can be dispensed with as a support.

The invention shall now be described with reference to preferred embodiments:

Two preferred polymer materials with a medicamentous depot effect were produced according to the method of the invention. Other compositions are thereby not excluded.

The following composition of the starting materials was used:

|  | Amount (weight percent) |
|---|---|
| Natural rubber | 37.17 |
| chalk | 46.47 |
| curing activator[1] | 1.49 |
| molecular sieve/medicament adduct[2] | 14.87 |
| and |  |
| silicone rubber | 52.6 |
| chalk | 31.6 |
| molecular sieve/medicament adduct[2] | 15.8 |

[1]Trimethylolpropane trimethacrylate
[2]Molecular sieve 13X / pentosan polysulfate After mixing of the starting materials in conventional mixing methods, the mixture was formed by way of extrusion into a desired shape, e.g. into a tube.

After the mixture molding process had been terminated, the molded polymer material was sealed within a protective packaging of a polyamide film. Such an early packaging process is possible, as the used mixture is sufficiently stable, thus maintaining its shape. The product can be sold in such a packaging after finishing and can be stored until use. Subsequently, the packaged product was inserted into a metal mold of, for instance, aluminum or copper. Such a metal mold supports the removal of heat during the subsequent process steps.

The polymer material sealed within the polyamide film was radiated with β-rays. The polymer material was simultaneously cured and sterilized owing to this electron radiation. The material was consequently finished in one process step, and the additional sterilization step required in the prior art could be dispensed with.

The radiation dose used in said Examples was 33 KGy and 66 KGy, respectively, at a radiation duration of 20 sec.

Subsequently, proof was furnished of the biological activity as follows:

A defined amount of polymer material with a medicamentous depot effect was incubated in 4 ml of human citrate plasma at 37° C. The length of the thrombin time was determined in response to the incubation time.

The results are shown in the following table:

| | Thrombin time after introducing polymer material with a medicamentous effect into human citrate plasma | |
|---|---|---|
| Incubation time | Prolongation of the thrombin time | |
| (min) | sec | % |
| 0 | 28 | 187 |
| 30 | 34 | 227 |
| 60 | 38 | 253 |
| 120 | 40 | 267 |
| 180 | 41 | 273 |
| 240 | 44 | 293 |
| 300 | 49 | 327 |

These values were compared with the direct injection of heparin thrombin time was 100% at 15 sec.

It has been found that the polymer material with the medicamentous effect according to the present invention led to an essential prolongation of the thrombin time in comparison with the conventional injection method.

We claim:

1. A method for producing a polymer product from a polymer material with a medicamentous depot effect comprising the steps of:

mixing as starting materials a polymer material and a biologically active substance to form a mixture;

shaping the mixture into a molded shape;

placing the resultant molded shape into a protective packaging; and curing and sterilizing said molded shape in said protective packaging to form said polymer product having a medicamentous depot effect.

2. The method of claim 1, wherein the curing and sterilizing are performed through electron radiation.

3. The method of claim 2, wherein the curing and sterilizing are performed with radiation doses of from 10 to 120 KGy.

4. The method of claim 3, wherein the curing and sterilizing are performed with radiation doses of from 20 to 66 KGy.

5. The method of claim 2, wherein at least one substance which acts as an activator or curing agent is added to said polymer material for reducing the radiation dose of the electron radiation.

6. The method of claim 5, wherein the substance is an acrylate or a derivative thereof.

7. The method of claim 6, wherein the substance is trimethylolpropane trimethacrylate.

8. The method of claim 5, wherein the substance is added in an amount of from 0 to 20% by weight.

9. The method of claim 8, wherein the substance is added in an amount of from 0 to 5% by weight.

10. The method of claim 1, wherein the polymer material is a natural and/or synthetic polymer.

11. The method of claim 1, wherein the biologically active substance is bound to an inorganic or organic carrier prior to mixing with said polymer material.

12. The method of claim 11, wherein the carrier is a molecular sieve and/or layered silicate.

13. The method of claim 1, wherein the biologically active substance is a high-and/or low-molecular heparin or heparinoid.

14. The method according to claim 1, wherein said molded shape is placed in a heat-conducting mold after being placed into said protective packaging and prior to curing and sterilizing.

15. The method of claim 14, wherein said heat-conducting mold is a metal mold.

16. The method of claim 1, wherein the starting materials comprise natural or synthetic polymers in an amount of from 20 to 80% by weight, chalk or other suitable natural or synthetic fillers in an amount of from 0 to 80% by weight, curing activators in an amount of from 0 to 5% by weight and the biologically active substance comprises a carrier and medicament in an amount of from 1 to 50% by weight.

17. The method of claim 16, wherein the starting materials also include suitable dyes and polymer processing additives.

18. The method of claim 16, wherein the starting materials comprise natural rubber in an amount of 37.17%, chalk in an amount of 46.47%, curing activators in an amount of 1.49% and a molecular sieve/medicament adduct in an amount of 14.87%.

19. The method of claim 16, wherein the starting materials comprise silicone rubber in an amount of 52.6%, chalk in an amount of 31.6% and a molecular sieve/medicament adduct in an amount of 15.8%.

* * * * *